US00PP28099P2

(12) United States Plant Patent
Wood

(10) Patent No.: US PP28,099 P2
(45) Date of Patent: Jun. 13, 2017

(54) ***LAGERSTROEMIA* 'SMLIPURPLE101'**

(50) Latin Name: ***Lagerstroemia* cultivar**
Varietal Denomination: SMLIPURPLE101

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 14/998,759

(22) Filed: Feb. 9, 2016

(51) Int. Cl.
*A01H 5/00* (2006.01)

(52) U.S. Cl.
USPC ..... Plt./252

(58) Field of Classification Search
USPC ..... Plt./252
See application file for complete search history.

*Primary Examiner* — Annette Para
(74) *Attorney, Agent, or Firm* — Cassandra Bright

(57) ABSTRACT

A new and distinct *Lagerstroemia* cultivar named 'SMLIPURPLE101' is disclosed, characterized by early flowering of vibrant purple blooms, compact plant stature and good branching. Plants are floriferous. The new variety is a *Lagerstroemia*, normally used for ornamental horticulture purposes.

1 Drawing Sheet

SUMMARY OF THE INVENTION

The cultivar 'SMLIPURPLE101' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMLIPURPLE101' These characteristics in combination distinguish 'SMLIPURPLE101' as a new and distinct *Lagerstroemia* cultivar:

1. Vibrant purple flowers.
2. Early flowering.
3. Very floriferous plants.
4. Compact plant stature.
5. Plants with good branching.

Plants of the new cultivar 'SMLIPURPLE101' are similar to plants of the seed parent, *Lagerstroemia* 'Violet Filli' in most horticultural characteristics, however, plants of the new cultivar 'SMLIPURPLE101' differ in the following;

1. Plants of the new variety are taller and more open in habit.
2. Flowers of the new variety are darer and brighter purple. The comparator has lighter lavender flowers.

COMMERCIAL COMPARISON

Plants of the new cultivar 'SMLIPURPLE101' are comparable to the patented commercial variety *Lagerstroemia* 'Early Bird Purple' U.S. Plant Pat. No. 22,718. The two *Lagerstroemia* varieties are similar in most horticultural characteristics; however, the new variety 'SMLIPURPLE101' differs in the following:

1. Darker/brighter purple. The comparator has lighter purple flowers.

BRIEF DESCRIPTION OF THE PHOTOGRAPH

The accompanying photograph in FIG. 1 illustrates in full color a typical plant of 'SMLIPURPLE101' grown in a greenhouse in Grand Haven Mich. Age of the plant photographed is approximately 2 years old from a rooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart sixth 2015 except where general terms of ordinary dictionary significance are used. The following observations and measurements describe 'SMLIPURPLE101' plants grown in a poly house during Summer of 2015 in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Lagerstroemia indica* 'SMLIPURPLE101'.

PROPAGATION

Type of propagation typically used: Terminal vegetative cutting.

Time to initiate roots: About 14-21 days 24° C.

Time to produce a rooted cutting: About 30-40 days at 24° C.

Root description: Thin, fibrous, not fleshy, freely branching. White in color, not accurately measured with RHS Chart.

PLANT

Age of plant described: 2-3 years old from rooted cutting.

Container size: 3 gallon container.

Overall plant shape: Upright.

Growth habit: Freely branching outward.

Plant spread: 76 cm.

Plant height: 95 cm.
Growth rate: Strong.
Plant vigor: Good.
Branching habit: Basal, some pinching required.
Length of primary lateral branches: 70 cm.
Diameter of lateral branches: 1.3 cm.
Quantity of lateral branches: 7.
Stem:
*Color*.—Near RHS Brown 200B blending upward to new growth of Yellow-green 145C blended with Red-purple 58A.
*Shape*.—Square shaped stem.
*Strength*.—Strong.
*Aspect angle*.—5-45°.
*Texture*.—Pubescent. Mature growth woody.
*Other*.—Stem color provides bold contrast to the foliage and flowers.
Internode length: 1.8 cm.

FOLIAGE

Leaf:
*Arrangement*.—Sub-opposite to alternate, single.
*Quantity*.—Approximately 20 to 30 per main branch.
*Average length*.—New growth: 1.6 cm Old Growth: 5 cm.
*Average width*.—New growth: 0.75 cm Old Growth: 2.5 cm.
*Shape of blade*.—Lance-ovate.
*Apex*.—Acute.
*Base*.—Rounded.
*Margin*.—Entire.
*Texture of top surface*.—Smooth, waxy.
*Texture of bottom surface*.—Smooth, waxy.
*Color*.—Young foliage upper side: Near RHS Green 141B with Greyed-purple 187C along margin. Young foliage under side: Near RHS Green 141C with Greyed-purple 187C along margin. Mature foliage upper side: Near RHS Green 137A. Mature foliage under side: Near RHS Green 141C.
*Venation*.—Type: Pinnate. Venation color upper side. Near RHS Greyed-purple 187C. Venation color under side: Near RHS Yellow-green 145B.
*Petiole*.—Average Length: 2 mm. Diameter: 1 mm. Color: Upper: Near RHS Yellow-green 145B blended with Red-purple 60A. Lower: Near RHS Yellow-green 145B. Texture upper and lower: Smooth, coriaceous.

FLOWER

Natural flowering season: June through October.
Flower arrangement: Terminal panicles.
Inflorescence form: Panicles.
Quantity of flowers per inflorescence: Average 24 open flowers and approximately 20 to 6 buds.
Inflorescence size:
*Width*.—14 cm.
*Height*.—15 cm.
Individual flowers:
*Shape*.—Rotate whorl of 6 freely attached petals.
*Habit*.—Whorled outward.
*Diameter*.—3.5 cm.
*Length*.—4.3 cm.
*Depth*.—1.5 cm.
*Aspect*.—Upright, outward.
*Persistence*.—Self cleaning.
*Fragrance*.—Slight to no scent.
Petals:
*Arrangement*.—Whorled, not fused.
*Number*.—6.
*Shape*.—Orbicular.
*Margin*.—Irregular undulate.
*Tip shape*.—Rounded.
*Base shape*.—Rounded.
*Length*.—Average 1.4 cm.
*Width*.—Average 1.1 cm.
*Texture*.—Upper: Soft, smooth, somewhat papery. Lower: Soft, smooth, somewhat papery.
Color:
*When opening*.—Upper surface: Near RHS Purple 77A. Under surface: Near RHS Purple 77A.
*Fully opened*.—Upper surface: Near RHS Purple 77A. Under surface: Near RHS Purple 77A.
*Fading*.—Upper surface: Near RHS Purple 77A. Under surface: Near RHS Purple 77A.
Bud:
*Shape*.—Obovate.
*Length*.—6.5 mm.
*Diameter*.—6.5 mm.
*Color*.—Near RHS Red-purple 58A blended with Greyed-green 194B.
Sepals:
*Appearance*.—Healthy, variations of color.
*Arrangement*.—Unguiculate.
*Shape*.—Narrowly triangular.
*Tip shape*.—Acute.
*Base shape*.—Obtuse.
*Margin*.—Entire.
*Quantity per flower*.—6.
*Length*.—5 mm.
*Width*.—4 mm.
*Margin*.—Entire.
*Texture*.—Upper: Smooth, coriaceuus, rugose. Lower: Smooth.
*Color*.—Upper and lower: Near RHA Yellow-green 145C blended with Red-purple 60A.
Calyx:
*Shape*.—Unguiculate.
*Length*.—5 mm.
*Diameter*.—5 mm.
Peduncle:
*Length*.—1 cm.
*Diameter*.—0.5-1 mm.
*Texture*.—Smooth.
*Color*.—Near RHS Yellow-green 145B blended with Red-purple 60A.
*Orientation*.—Upright and outward.
*Strength*.—Good.
Pedicel:
*Length*.—9 mm.
*Diameter*.—0.5-1 mm.
*Angle*.—5-35°.
*Strength*.—Good.
*Texture*.—Smooth.
*Color*.—Near RHS Yellow-green 145B blended Red-purple 60A.

REPRODUCTIVE ORGANS

Stamens:

*Number.*—*About* 30.

*Filament length.*—0.8-1.8 cm.

*Filament color.*—Near RHS Red-purple 63A.

Anthers:

*Shape.*—Orbital.

*Length.*—1 mm.

*Color.*—Near RHS Yellow-orange 15B.

*Pollen.*—Color: Near RHS Yellow 12B. Quantity: Good.

Pistil:

*Number.*—1.

*Length.*—1.85 mm.

*Style.*—Length: 1 cm. Color: Near RHS Red 53B.

*Stigma.*—Shape: Globe. Color: Near RHS Yellow-green 152B. Ovary color: Near RHS Yellow 11B.

OTHER CHARACTERISTICS

Disease/pest resistance: Neither resistance nor susceptibility to normal diseases of *Lagerstroemia.*

Garden performance: Good tolerance of environmental stressors, noted to perform well in harsh winters.

What is claimed is:

1. A new and distinct cultivar of *Lagerstroemia* plant named 'SMLIPURPLE101' as herein illustrated and described.

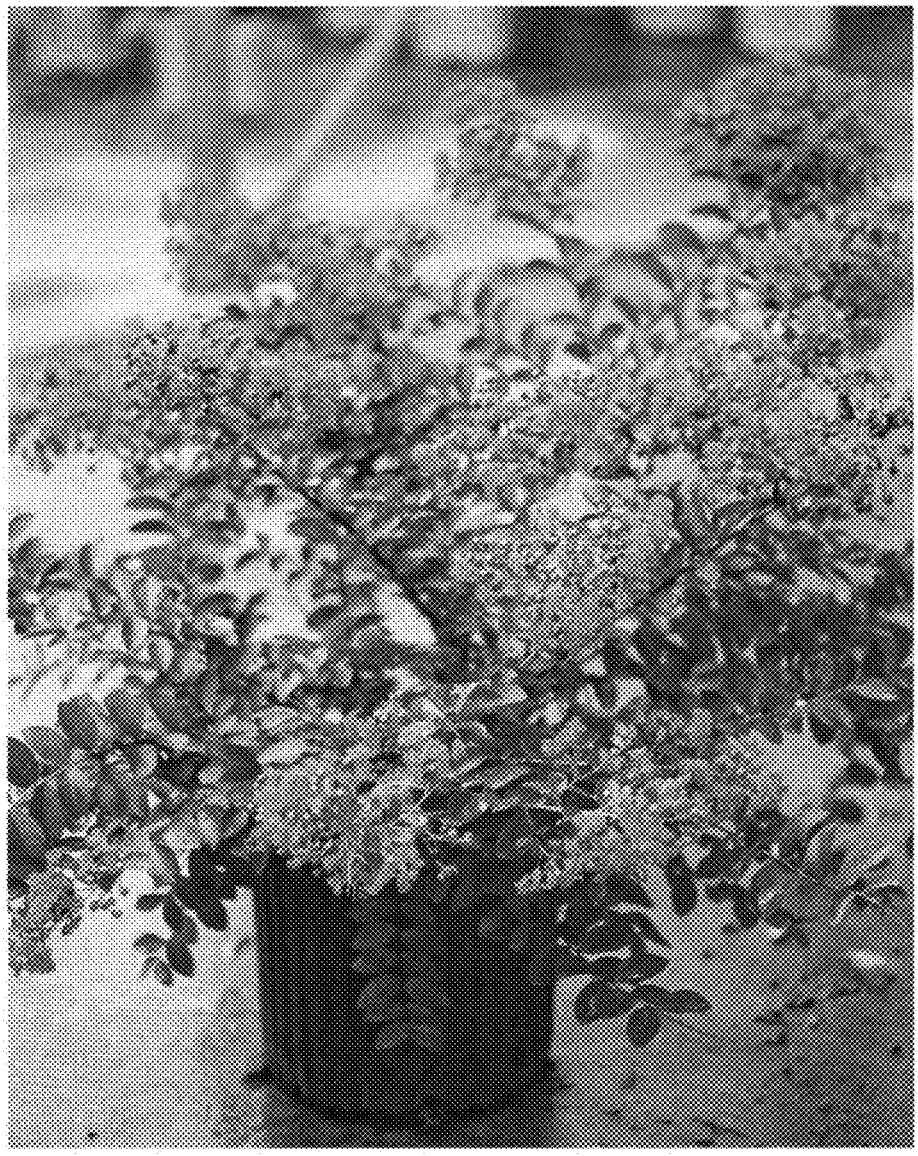

* * * * *